United States Patent [19]

DeCote, Jr.

[11] Patent Number: 4,674,509
[45] Date of Patent: Jun. 23, 1987

[54] SYSTEM AND METHOD FOR DETECTING EVOKED CARDIAC CONTRACTIONS

[75] Inventor: Robert DeCote, Jr., Miami Beach, Fla.

[73] Assignee: Cordis Corporation, Miami, Fla.

[21] Appl. No.: 738,607

[22] Filed: May 28, 1985

[51] Int. Cl.⁴ .............................................. A61N 1/36
[52] U.S. Cl. ............................... 128/419 PT; 128/697
[58] Field of Search ................... 128/419 PG, 419 PT, 128/697

[56] References Cited

U.S. PATENT DOCUMENTS

| 3,757,790 | 9/1973 | Herrmann . | |
|---|---|---|---|
| 3,777,762 | 12/1973 | Nielsen . | |
| 3,800,801 | 4/1974 | Gaillard . | |
| 4,144,892 | 3/1979 | Averbach | 128/419 PT |
| 4,245,643 | 1/1981 | Benzing, III et al. . | |
| 4,290,430 | 9/1981 | Bihn et al. . | |
| 4,337,776 | 7/1982 | Daly et al. . | |
| 4,537,201 | 8/1985 | Delle-Vedove et al. | 128/419 PG |

FOREIGN PATENT DOCUMENTS

| 2701234 | 7/1978 | Fed. Rep. of Germany ...... 128/419 PG |
| 160210 | 5/1983 | German Democratic Rep. ............................ 128/419 PG |
| 825098 | 4/1981 | U.S.S.R. ........................ 128/419 PG |

OTHER PUBLICATIONS

A New Electronic System for the Detection of the Stimulated Cardiac Response, J. Mugica, B. Lazarus, D. Delle-Vedove, Y. Lallemand, O. Hubert.

Primary Examiner—William E. Kamm
Attorney, Agent, or Firm—Lockwood, Alex, FitzGibbon & Cummings

[57] ABSTRACT

A system and method for detecting evoked cardiac contractions applies pacing pulses to a patient's heart while simultaneously monitoring intracardiac electrical activity to detect evoked cardiac contractions. Pacing pulses are generated in pairs such that at most only one pulse of each pair can induce capture. The lead recovery waveforms produced in response to each of the pulses within a pair are electronically subtracted to yield a difference signal indicative of induced cardiac response.

13 Claims, 10 Drawing Figures

SYSTEM AND METHOD FOR DETECTING EVOKED CARDIAC CONTRACTIONS

BACKGROUND OF THE INVENTION

The present invention relates generally to cardiac pacing systems, and more particularly to a system and method for detecting cardiac contractions induced in response to the application of pacing pulses to a patient's heart.

While a variety of well known systems and methods exist for electronically detecting the naturally occurring contractions of a patients heart, the direct detection of externally induced cariac contractions has presented a significant technical challenge for which no completely satisfactory answer has yet been developed. Direct detection of an evoked cardiac response is frequently frustrated by the presence of strong pacing pulses which greatly exceed the magnitude of the cardiac signal to be detected. Cardiac event sense amplifiers are often saturated by such pulses and are thus rendered insensitive over a period of time during which induced cardiac response events most often occur. This particular difficulty has been largely overcome by the development of unsaturable, fast-recovery sense amplifiers such as that described by the present inventor in his copending application Ser. No. 738,608 entitled "Unsaturable Sense Amplifier for Pacer System Analyzer", filed concurrently herewith.

The direct detection of evoked cardiac response events has been further complicated by the presence of large post-pulse lead recovery artifacts which result from depolarization of the interface between a pacing lead and the adjacent cardiac tissue. Such recovery artifacts, which typically exceed the level of evoked cardiac response signals by several orders of magnitude, frequently mask the much lower level, and shorter duration, response signals which indicate the occurrence of induced cardiac events. Additionally, the large slew voltages developed by such artifacts require considerable system dynamic range, which is difficult to provide in a system intended to detect typically low-level induced cardiac response voltages.

One prior technique for directly detecting cardiac response signals involved the application of a post-pacing pulse reverse current to a pacing lead in order to more rapidly depolarize the lead-cardiac interface. This technique found application as a palliative, but as an "exact" lead depolarization technique suffered from the fact that charge discharge time constants are non-linear functions of pacer drive level, lead type, lead geometry, and time-modulated lead impedance. In addition, owing to the anodic voltages required, this approach introduced the possibility of inducing lead deterioration through corrosion.

Another prior technique was based on the observation that lead recovery artifacts correspond generally to the exponential decay characteristics of a resistor-capacitor network. Accordingly, in this sytem, the antilog of the post-pulse signal was computed in order to recover what approximated the induced cardiac response. The accuracy of this system was inherently limited by the degree to which the lead recover artifacts departed from simple exponentials.

By contrast, the present invention is directed to a system and method for directly detecting cardiac contractions induced in response to application of pacing pulses to a patient's heart. The system effectively detects the actual cardiac response signal in the presence of both the applied pacing pulses and the subsequent resulting lead recovery artifacts. This system can be used with any cardiac lead configuration such as unipolar, bipolar, tripolar, etc., with any of the currently used lead materials such as platinum, elgiloy, etc., and with any of the lead tip geometries such as screw-in, ball-tip, parabolic, etc.

The system and method are particularly well adapted for use in a pacer system analyzer, wherein the operation of a cardiac pacer is evaluated in association with a patient's heart prior to implantation. By using a pacer system analyzer, a physician is able to tailor the operating parameters of a pacer system as required for the specific needs of an individual patient before the pacer has been fully implanted and the implantation surgery completed. The system and method of the present invention, when incorporated into a pacing system facilitates the measurement of a patient's capture threshold, which represents the minimum pace output level required to reliably stimulate cardiac contractions.

In view of the foregoing, it is a general object of the present invention to provide a new and improved system and method for detecting the occurrence of cardiac events It is a further object of the present invention to provide a system and method for directly detecting the occurrence of evoked cardiac contractions.

It is still another object of the present invention to provide an improved system for promptly, accurately, conveniently and reliably determining the capture threshold of a patient's heart.

SUMMARY OF THE INVENTION

A system for detecting cardiac contractions induced in response to application of pacing pulses to a patient's heart, includes means for generating a series of pacing pulse pairs individually comprising two pacing pulses separated in time by less than the refractory period of the patient's heart muscle, and means for detecting electrical artifacts produced in response to the application of the pulses to the patient's heart. Means are provided for comparing the net artifacts following each of the pulses within individual ones of the pairs to determine whether cardiac contraction has occurred in response to application of a particular pacing pulse pair to the patient's heart.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
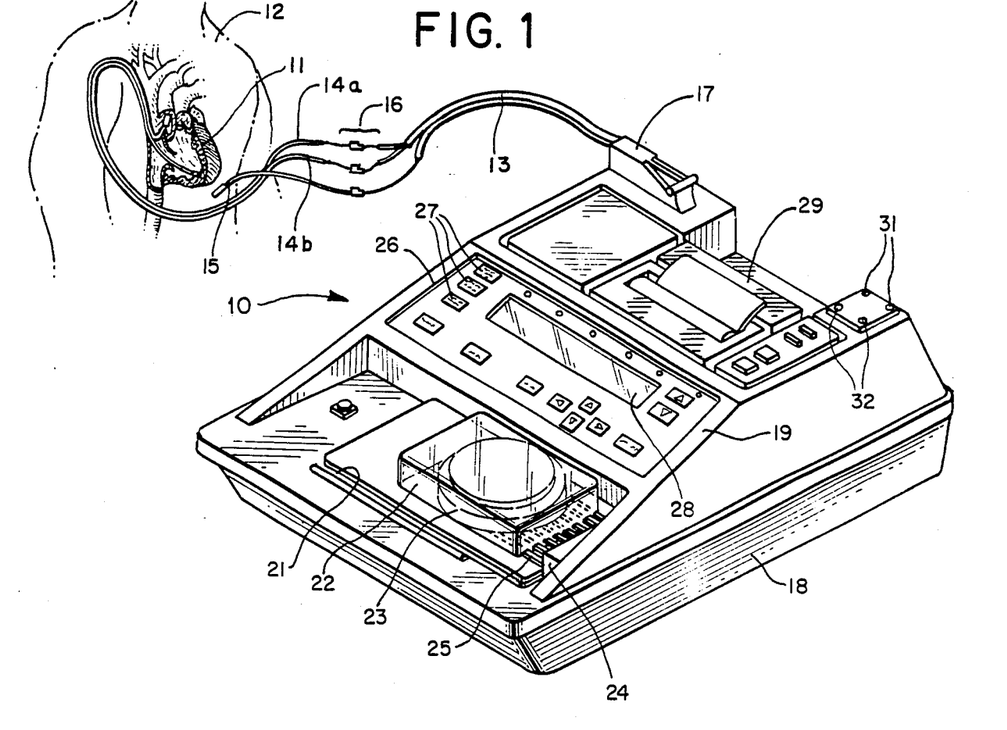
FIG. 1 is a perspective view of a pacer system analyzer incorporating a system for detecting evoked cardiac contractions constructed in accordance with the invention.

Referring to the Figures, and particularly to FIG. 1, a pacer system analyzer (PSA) 10 is shown which incorporates a system for detecting evoked cardiac contractions constructed in accordance with the invention. As illustrated, the PSA is connected to the heart 11 through a patient cable assembly 13 and a pair of unipolar atrial and ventricular pacing leads 14, 15 which have been implanted in the patient's heart in known manner. Alternately, bipolar pacing leads can be used when appropriate. One end of patient cable 13 is connected to the accessible ends of pacing leads 14 and 15 through a plurality of electrical clips 16 of known construction. The remaining end of the patient cable assembly is electrically connected to PSA 10 by means of a molded multi contact connector 17.

PSA 10 is contained within a generally rectangular housing 18 formed of a durable, insulating plastic or like material and includes a sloping, generally flat, control panel 19. A portion of the housing is formed to provide a guide 21 for receiving a sealed package 22 containing a sterile implantable cardiac pacer 23. A connector 24 engages a plurality of electrical contacts 25 formed on package 22 to provide electrical communication between PSA 10 and implantable pacer 23. Panel 19 includes a user keyboard 26 having a plurality of pressure sensitive user-actuable push button controls 27 and a liquid crystal display (LCD) 28.

PSA 10 operates in one of several user-selected modes in accordance with entered keystroke commands. To assist the user in selecting the appropriate operating mode, a series of internally generated instructions and a plurality of measured pacer system parameters are displayed on LCD 28. A printer/plotter mechanism 29 provides a printed record of measured pacer system operating parameters and measured patient parameters, while two pairs of isolated electrogram (EGM) electrodes 31 and 32 provide electrically isolated atrial and ventricular intracardiac signals for safe connection to external instrumentation.

Heart 11, patient cable 13, leads 14a, 14b and 15, and pacer 23 together form a pacer system. This modality is referred to as pace-thru pacing. PSA 10 functions to automatically measure various parameters of this system and to thereby assist the physician in selecting implanting and programming the pacer system components for maximum effectiveness. Additionally, proper operation of the system can be verified before final implantation, and pacing pulses for supporting the patient during the pacer system implantation can be thus generated.

Figure 2:
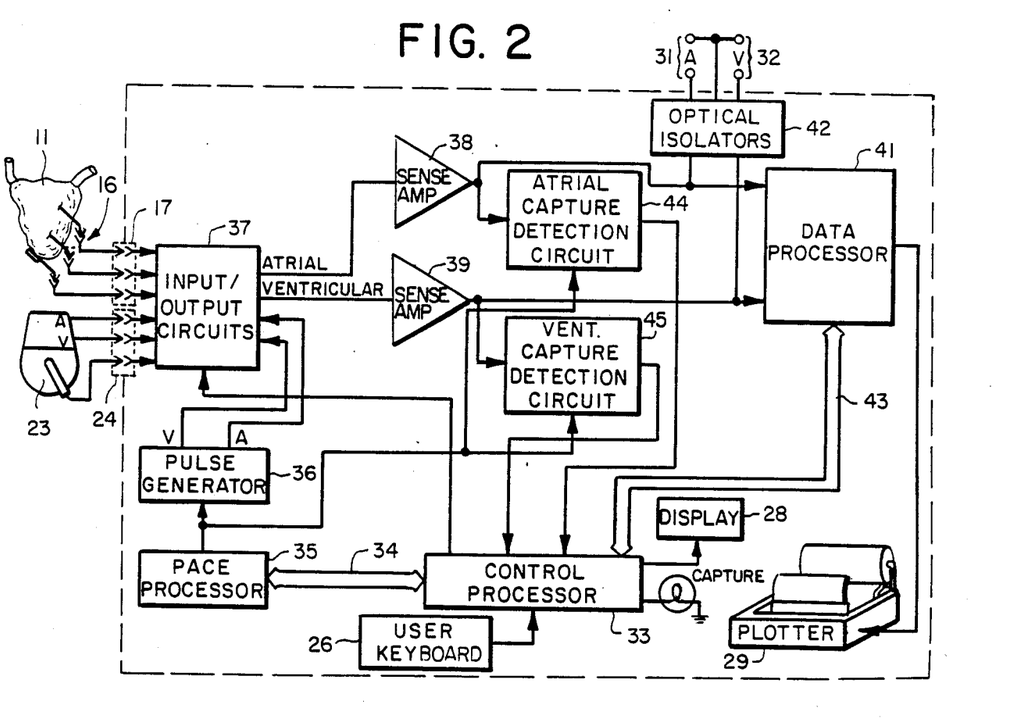
FIG. 2 is a simplified functional block diagram of the pacer system analyzer illustrated in FIG. 1 showing the principal subsystems thereof.

Referring to the simplified functional system block diagram of FIG. 2, PSA 10 is seen to include a control processor 33 which is preferably microprocessor based and which is programmed to generate a plurality of system control voltages in respons to user-entered keystroke commands from user keyboard 26. Control processor 33 is coupled through a data/control bus 34 to a microprocessor based pace processor 35 which in turn controls the generation of atrial and ventricular pacing pulses developed by a constant current or constant voltage pulse generator 36. Various parameters of the pacing pulses developed by pulse generator 36, such as pulse amplitude, pulse width, pulse spacing and pulse repetition frequency are specified by pace processor 35 in accordance with control voltages and gates from control processor 33.

Atrial and ventricular pacing pulses developed by pulse generator 36 are applied to an input/output interface circuit 37 which is connected to the patient's heart 11, and implantable pacer 23 through connectors 17 and 24, respectively. Interface 37 operates in accordance with control inputs from control processor 33 and serves to couple heart 11 to either the implantable pacer 23 or pulse generator 36 such that the heart can be paced exclusively by either the pacer 23 or the pulse generator 36 as desired.

In addition to the foregoing, interface 37 further serves to couple cardiac pacing leads 14a, 14b and 15 to the respective inputs of atrial and ventricular unsaturable sense amplifiers 38 and 39. Each of these amplifiers is preferably constructed in accordance with the pinciples described in the present inventor's copending application Ser. No. 738,608 entitled "Unsaturable Sense Amplifier for Pacer System Analyzer", filed concurrently herewith and is not saturated by the presence of the large pacing pulses and/or lead artifact voltages which are periodically applied to cardiac leads 14 and 15. Accordingly, each amplifier is capable of amplifying the residual artifacts which are produced some time after each pacing pulse.

The amplified atrial and ventricular artifact signals provided by amplifiers 38 and 39 are coupled to the respective inputs of a microprocessor based data processor 41 and to the respective inputs of an optical isolator 42. Isolator 42 provides atrial and ventricular electrogram signals and functions to electrically isolate the heart from any additional electrical instrumentation in order to enhance patient safety. Data processor 41 performs a variety of measurements and calculations on sensed atrial and ventricular signals and processes the resulting data in accordance with instructions from control processor 33 which are supplied to the data processor through a control/data bus 43. The results developed by such data processing are returned to control processor 33 for visual display on LCD 28, or are supplied to the plotter in order to provide a permanent record of pacer system measurements.

The outputs of sense amplifiers 38 and 39 are also connected respectively to the inputs of atrial and ventricular capture detection circuits 44 and 45 which have each been constructed in accordance with the present invention. The capture detection circuits function to sense the occurrence of cardiac contractions during a short period following each pacing pulse. When a contraction occurs immediately following the application of each pacing pulse, a capture condition is indicated and an appropriate capture indicative signal is returned to the control processor 33.

Figure 3:
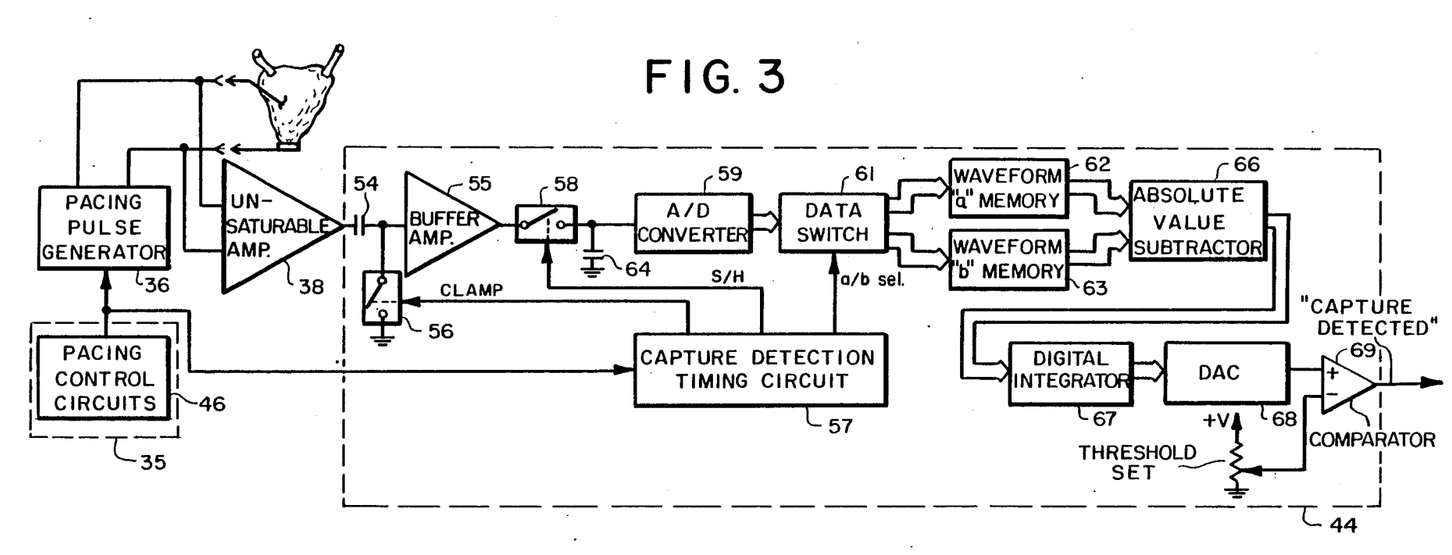
FIG. 3 is a simplified block diagram of the system for detecting evoked cardiac contractions incorporated in the pacer system analyzer of FIG. 1.

The operation of the system and method for detecting evoked cardiac contractions as implemented in each of the capture detection circuits 44 and 45 can be understood by reference to the block diagram of FIG. 3 and the waveforms of FIGS. 4-10. The operation of the system and method is based on the recognition that if pacing pulses are applied to the heart in pairs, and if the pulse spacing within each pair is less than the refractory period of the heart muscle, then, at most, only one pulse of each pair can induce cardiac capture. It has been experimentally determined that when the myocardium depolarizes, it becomes refractory for at least 150 milliseconds. Accordingly, pacing pulses generated in pairs spaced by a nominal 100 millisecond interval will, when applied to the heart, produce at most one contraction per pulse pair. (In order for both pacer pulses to evoke contractions calls for the possibility of pacing a human heart at 600 ppm. Even for infants, this is physiologically impossible.)

The operation of the system and method is further based on the observation that post-pulse lead recovery artifacts are essentially completely decayed within 50 to 75 milliseconds following the end of each pacing pulse, particularly in the vicinity of typical capture threshold levels. Accordingly, the lead recovery artifact waveforms produced in response to each pulse of pacing pulse pair will be essentially identical in the absence of any induced cardiac response event. Thus, a properly implemented waveform subtraction of the lead recovery curves will yield a near-zero result in the event neither pulse of a pair induces capture. However, if either pulse evokes a cardiac contraction, one pulse will have associated with it only the lead recover artifact whereas the other pulse will have associated with it the lead recovery artifact plus cardiac contraction signal. Accordingly, subtraction of the net recovery curves will produce a detectable waveform difference. Since contractions on both pulses of a pair has been ruled out, it can be safely assumed that an induced cardiac contraction will always result in a non-zero waveform difference.

FIG. 3 illustrates the atrial capture detection circuit 44 (or 45) in functional block diagram form. Since atrial response signals are typically smaller than their ventricular counterparts, and therefore much more difficult to detect, the system is preferably optimized to such atrial signals. Aside from possible modification of various adjustable threshold settings, the design, construction and operation of the atrial and ventricular capture detection circuits is identical.

Figure 4:
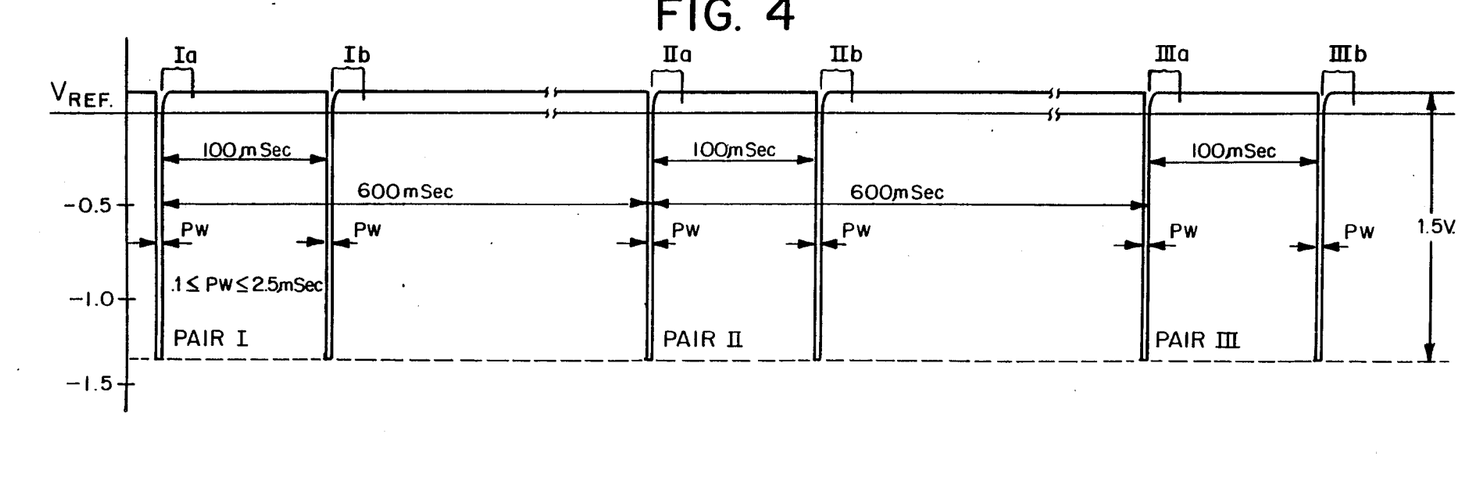
FIGS. 4-10 are a series of waveform depictions useful in understanding the operation of the system illustrated in FIG. 3.

In accordance with one aspect of the invention, the pace processor 35 includes pacing control circuits 46 which condition the pacing pulse generator 36 t produce pacing pulses in pairs as illustrated in FIG. 4. As shown, each pacing pulse consists of a negatively going rectangular pulse having a representative nominal magnitude of 1.5 volts and having a pulse width (PW) ranging typically between 0.1 and 2.5 milliseconds. By way of illustration, the individual pulses are grouped in pairs spaced from one another by 600 millisecond intervals giving a nominal cycle rate of 100 pairs per minute. Three such pairs are illustrated and are designated by reference characters I, II and III, respectively. Within each pair, pulses are spaced by a 100 millisecond interval.

As can be observed by further reference to FIG. 4, the trailing edge of each pacing pulse is not rectangular but, rather, includes a substantial lead recovery artifact having the general form associated with exponential voltage decay. Any cardiac response signals developed in the immediate post-pulse interval are therefore superimposed on the lead recovery artifact. Since the magnitude of such cardiac response signals may be on the order of a few millivolts, it will be appreciated that the presence of the relatively large lead recovery artifacts complicates the detection of such signals. These response signals, if any, will occur during discrete intervals following each pulse. These intervals, identified as $I_a$, $I_b$, $II_a$, $II_b$, $III_a$, and $III_b$, contain a substantial lead recovery artifact component in addition to any possible cardiac response signals.

FIGS. 5-10 depict, in enlarged form, the portions of the waveforms illustrated in FIGS. 4 which may contain cardiac response information. As illustrated, the waveforms identified by reference character I, are those which result when neither pulse of a pulse pair induces a cardiac contraction. Similarly, the waveforms indicated by reference character II are those which result when the first pulse of a pulse pair evokes capture. Finally, the waveforms designated by reference character III are those which result when the second pulse of a pair induces capture. In each waveform, the subscript "a" corresponds to the first pulse of a pulse pair, while the subscript "b" corresponds to the second pulse of the pair.

Figure 5:
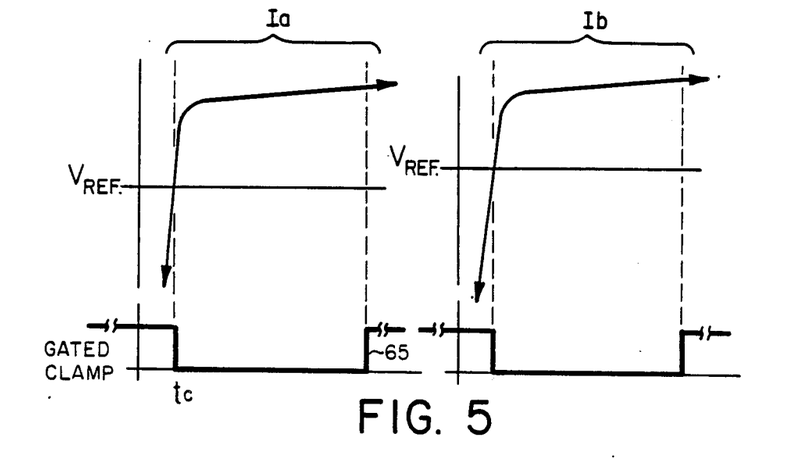
Figure 8:
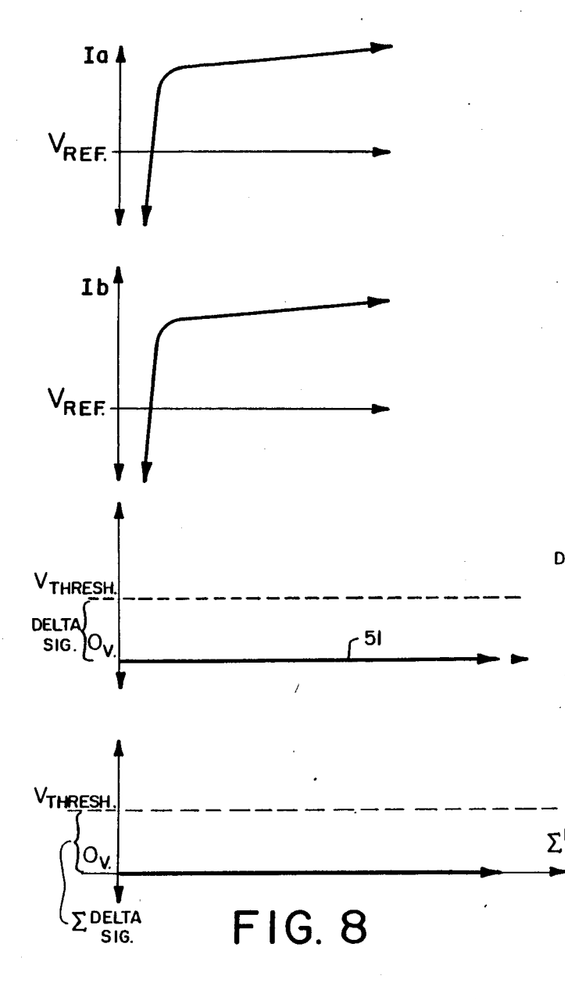

FIGS. 5 and 8 depict recovery waveforms $I_a$ and $I_b$ which result when neither pulse of a pulse pair induces a cardiac contraction. Since the artifact following the first pulse has fully expired by the time the second pulse is generated, the pre-pulse states are essentially identical and accordingly waveforms $I_a$ and $I_b$ are also essentially identical. Accordingly, when the waveforms are subtracted as illustrated in FIG. 8, the resulting difference signal 51 is substantially zero.

Figure 6:
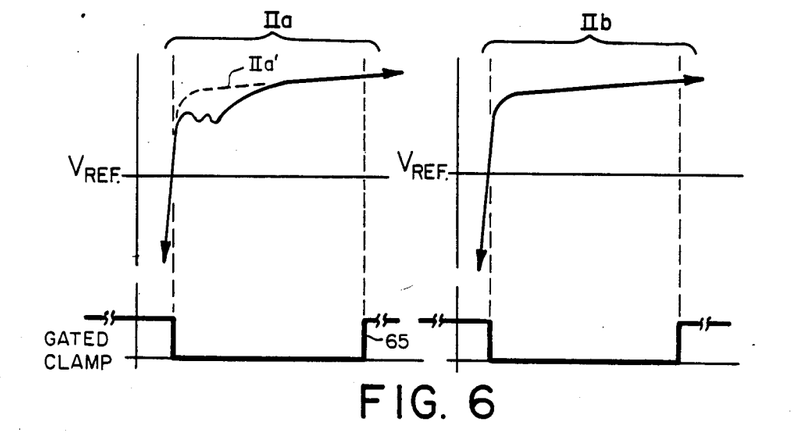
Figure 9:
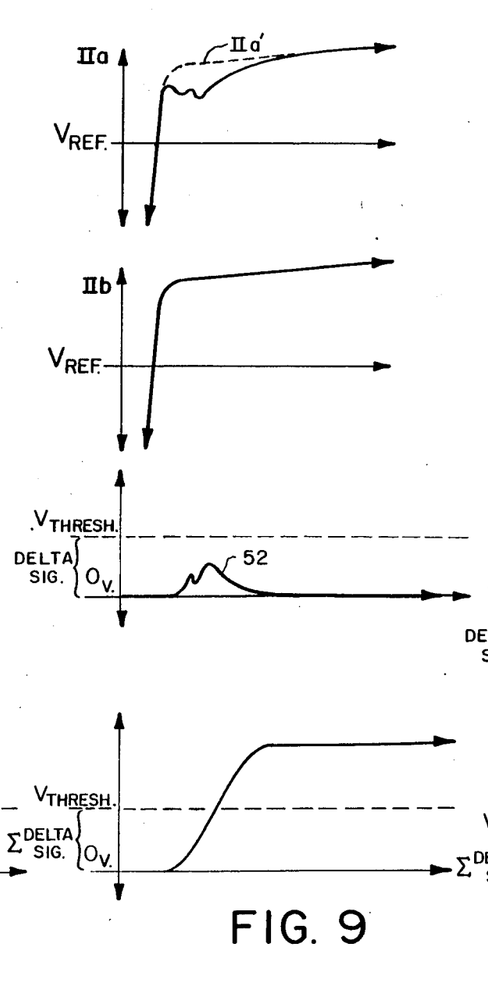

In FIGS. 6 and 9, the first pulse of an applied pulse pair has induced a cardiac contraction while the second pulse of the pair has not. Accordingly, waveform $II_a$ differs slightly from the waveform which would be obtained had the contraction not occurred. Such a baseline is illustrated in phantom in FIG. 6 as waveform $II_a'$ and is seen to correspond generally to waveform $II_b$ obtained following the second pulse of the pair. Accordingly, when waveforms $II_a$ and $II_b$ are subtracted as illustrated in FIG. 9, a non-zero difference signal 52 is produced which generally replicates the evoked cardiac response signal itself. Thus, when a substantial difference signal is developed, a capture condition is indicated.

Figure 7:
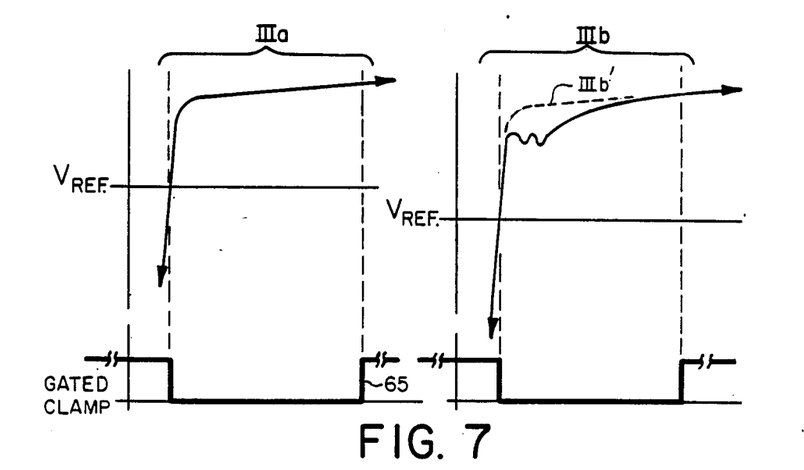
Figure 10:
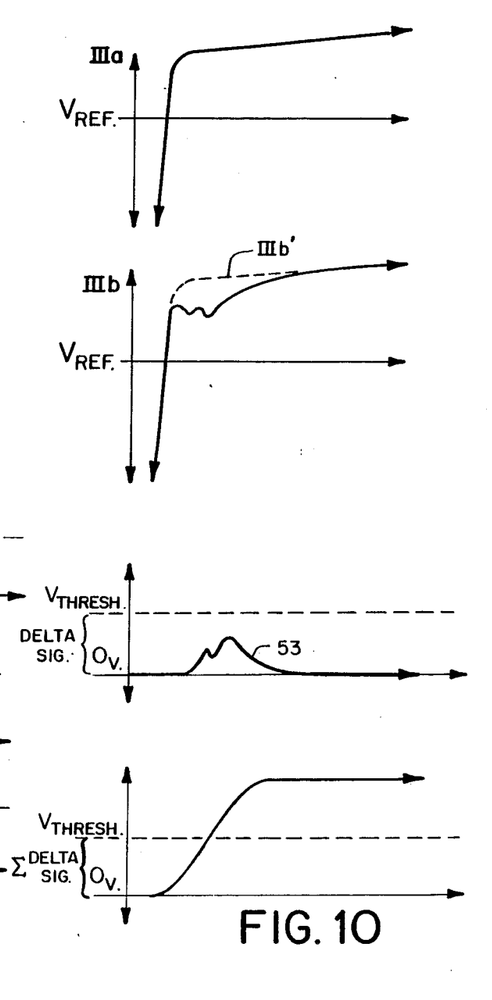

FIGS. 7 and 10 correspond generally to FIGS. 6 and 9 except that in these figures it is the second pulse of the pair which induces a cardiac contraction. Accordingly, waveform $III_b'$ (FIG. 7 and 10) depicts the waveform which would have been obtained had the cardiac contraction not occurred, while waveform 53 (FIG. 10) results when waveforms $III_a$ and $III_b$ are properly subtracted and corresponds generally to the cardiac response signal produced during the evoked contraction.

The system illustrated in FIG. 3 is arranged to perform the required absolute value waveform subtraction and provides at its output a "CAPTURE DETECTED" signal when a cardiac contraction occurs in response to the application of a pacing pulse pair.

The output of unsaturable sense amplifier 38 is applied through capacitor 54 to the input of buffer amplifier 55. The input of buffer amplifier 55 is also connected through a voltage controlled analog switch 56 to circuit ground. This constitutes voltage clamping to ground potential so that as pacer energy is changed, the reference point at $t_c$ (FIG. 5) is always initially zero volts. Biasing circuitry within the buffer amp ifier 55 offsets this for optimal location within the input range of ADC (59). A control voltage for controlling the operation of the clamp (56) switch is developed by a capture detection timing circuit 57 which is coupled to the pacing control circuits 46 of the pace processor 35, and which develops a series of additional control voltages for controlling the timing and operation of the capture detection circuit.

The output of buffer amplifier 55 is connected through sample-and-hold voltage controlled switch 58 to a holding capacitor 64 and to the input of an analog-to-digital converter (ADC) 59, the output of which is coupled through a two-position data switch 61 to either of two digital waveform RAM type memories 62 or 63. Control voltages for controlling switches 58 and 61 are also developed by the capture detection timing circuit 57. A capacitor 64 is connected between the input of analog-to-digital converter 59 and circuit ground, and, together with switch 58, forms a sample and hold circuit having a sampling rate controlled by the capture detection timing circuit 57.

Capacitor 54 and switch 56 together form a gated clamp which operates under the control of the capture detection timing circuit. Switch 56 closes when a logic-high gated clamp control signal is developed by the capture detection timing circuit, and opens when the gated clamp control voltage is logic-low. The gated clamp control signal is indicated as waveform 65 in each of FIGS. 5, 6 and 7.

The timing of the gated clamp control signal is such that switch 56 is made to close from just before each output pacing pulse, until a few milliseconds thereafter, with the effect that the heaviest pacer pulse artifacts are not felt by buffer amplifier 55. While switch 56 is closed, capacitor 54 will be dynamically charged to the instantaneous output voltage of amplifier 38. Accordingly, immediately after the switch opens, the input to the buffer amplifier 55 will be zero volts. At that moment, capacitor 54 will be charged t the instantaneous value of amplified lead recovery voltage, $V_{ref}$, in FIGS. 4 through 10. Therefore, the initial voltage applied to the input of buffer amplifier 55 at the instant the switch opens will be equal to ground potential, and any subsequent change in the output voltage of unsaturable amplifier 38 will appear as an identical change relative to ground at the input of the buffer amplifier 55. This gated clamping action therefore serves to assure that the full dynamic range of ADC 59 is always utilized since no matter what the amplified lead recovery voltage, $V_{ref}$ of sense amplifier 38 is, the input voltage to buffer amplifier 55 will initially be zero volts and will change from that potential in strict accordance with subsequent changes in the sense amplifier output voltage.

The effect of the gated clamp can be visualized by reference to the waveforms of FIGS. 4-10. The reference potential forming the horizontal $V_{ref}$ axis is defined as the instantaneous lead recovery voltage existing at the instant the gated clamp control signal drops from logic-high to logic-low. This assures that any DC components of the recovered waveforms, which will vary according to pacing pulse level and lead type, are automatically compensated. Thus, no matter what the actual lead recovery voltage, the gated clamp assures that the reference potential will at all times commence from ground potential at the instant switch 56 opens.

During the period in which switch 56 is open, the output of buffer amplifier 55 is converted to a series of digitally encoded data words (bytes) by means of solid state switch 58, capacitor 64 and ADC 59. The sampling rate is controlled by the capture detection timing circuit 57 and is selected to provide an accurate digital representation of the output of the buffer amplifier. Thus, each of the lead response waveform signals depicted in FIGS. 5-7 will be converted to a corresponding string of weighted digital bytes.

From ADC 59, the byte stream is coupled through data switch 61 to either of the two waveform RAM memories 62 or 63. The capture detection timing circuit 57 controls the operation of data switch 61 so that at all times the recovery waveform developed in response to the first, or "a" pulse of the pacing pulse pair is stored in waveform "a" memory 62, while the waveform produced in response to the second, or "b" pulse of the pacing pulse pair is stored in waveform "b" memory 63. Thus, following the generation and application of each pacing pulse pair, waveform memory 62 and 63 will contain digitally encoded versions of the response waveforms produced in response to each pulse of the pair.

Following each pacing pulse pair, the respective bytes stored in waveform memory 62 and 63 are compared by means of a digital subtractor 66 which sequentially processes the corresponding bytes of the stored waveforms produced in response to the first and second pulses of each pulse pair and develops a new byte stream indicative of the absolute difference between the waveforms. This digital difference signal, which may be referred to as "delta", is then applied to the input of a digital integrator 67 having its ouptut coupled to a digital-to-analog converter (DAC) 68. DAC 68 converts the integrated "delta" signal to an analog voltage which can then be compared against a known threshold value by means of analog voltage comparator 69.

Since induced cardiac response signals are typically small compared with lead recovery artifacts, the difference signal "delta" due to an induced cardiac contraction will also be typically small. Accordingly, digital integrator 67 is preferably included in order to assure that any substantial non-zero "delta" signal is indeed due to an induced cardiac contraction. As illustrated in FIGS. 8-10, the integrated "delta" signal ultimately reaches a higher peak level than the peak "delta" level. Thus, the threshold voltage $V_{thresh.}$ can be set higher when integration is provided than it can in the absence of integration and accordingly, the possibility of producing false capture signals in response to random signal noise is greatly reduced. From another perspective, we see that if we used the Delta signal itself into the voltage comparator, we would be level sensitive. All positive slopes would be contributing towards threshold, but zero and negative slopes would not. However, by using the integrated Delta signal instead, we become area sensitive. In this case, the entire Delta area contributes towards threshold in a manner akin to "gathering experience" about the waveform. This improves the overall signal-to-noise characteristics of the capture detection syste and accordingly enhances discrimination between valid capture and no-capture conditions.

An analytic expression for the capture criterion is as follows:

CAPTURE CRITERION: $\sum_{1}^{n} |(a_n - b_n)| \geq V_{THRESH.}$

Where;
  n = number of sample points following $t_{clamp}$.
  $a_n$ = byte string values following a-pulse.
  $b_n$ = byte string values following b-pulse.

In an actual system constructed to implement the capture detection process, sense amplifier 38 and buffer amplifier 55 had voltage gains of X20 and X3 respectively, resulting in an overall system gain of X60. ADC 59 comprised an eight-bit converter referenced to a 5 volt line providing an inherent resolution of approximately 20 mV/step, or approximately 0.3 mV/step referred to the system input.

The pacing pulse generator was adjusted to develop pacing pulse pairs at intervals ranging between 300 and 2000 milliseconds, for an adjustable pulse pair rate of 30 to 200 pulse pairs per minute. Each pair, in turn, consisted of two electrically identical pulses spaced by a fixed 100 millisecond interval. Pulse width was adjustable between 0.1 and 2.5 milliseconds, in steps of 0.1 milliseconds.

In accordance with conventional pacemaker practice, a short circuit or "charge dump" interval was provided at the output of the pulse generator to reduce the magnitude and duration of the resulting lead recovery artifact. Accordingly, the capture detection timing circuit 57 was adjusted such that analog switch 56 of the gated clamp was closed just prior to the initiation of each pacing pulse and was kept closed for a period of 7 milliseconds following the termination of each output pulse. Buffer amplifier 55 thereby remained squelched during each pacing pulse, during each 4 millisecond charge dump period, and for an additional 3 milliseconds following each charge dump period in order that the active sample period include the time span between 7 and 22 milliseconds following the termination of each pacing pulse, which has been experimentally determined to contain the most significant evoked cardiac response waveforms.

It will be appreciated that the capability of detecting cardiac contractions induced in response to applied pacing pulses makes possible a system for conveniently ascertaining the minimum pulse energy level required to reliably evoke capture of a patient's heart. This minimum energy level, which is known as the cardiac capture threshold, can be conveniently ascertained by reducing the energy of the generated pacing pulses while simultaneously monitoring the output of the capture detection system. Operation at the capture threshold is indicated when each applied pacing pulse pair results in the generation of the "capture detected" signal at the output of the capture detection circuit, and when any decrease in pulse level energy results in less than a 100% correspondence between the application of pulse pairs and the generation of "capture detected" signals. When this condition is achieved, the patient's capture threshold is said to be equal to the corresponding pacing pulse energy to within the resolution of the system.

In order to provide the capability for determining capture threshold, pace processor 35 and pacing pulse generator 36 are preferably constructed to permit user-variation of the pacing pulse energy level. This permits the user to manually increase or decrease the pacing energy level, while simultaneously monitoring the cardiac response, in order to ascertain the minimum pacing energy required to reliably stimulate cardiac contractions.

It will be appreciated that, while discrete system components have been shown and described, the system may advantageously be implemented using microprocessor based circuitry in conjunction with suitable programming. Note that with such a system, the necessary numerical data processing (absolute value subtraction, integration, and threshold comparison) can be performed on a byte-by-byte basis during the lead recovery interval of the second pulse of each pulse pair. Furthermore, it will be appreciated that while specific puls levels and timing intervals have been referred to, these values have been provided for illustrative purposes and can be altered without departing from the scope or intent of the invention.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A method of detecting cardiac contractions induced in response to the application of pacing pulses to a patient heart having a predetermined minimum refractory period, comprising the steps of:
   applying a first pacing pulse to the patient's heart;
   detecting a first recovery artifact, indicative of cardiac activity, produced in response to application of said first pulse to the patient's heart;
   applying a second pacing pulse to the patient's heart withina time period following the application of said first pulse which is less than said minimum refractory period of the patient's heart;
   detecting the recovery artifact, indicative of cardiac activity, produced in response to application of said second pulse to the patient's heart; and
   comparing said first and second recovery artifacts to determine whether cardiac contraction has occurred in response to the application of either of said first or second pacing pulses.

2. The method of detecting induced cardiac contractions defined in claim 1 wherein said comparing said first and second recovery artifact signals comprises developing a difference signal indicative of the difference betweent the absolute values of said artifact signals, integrating the difference signal, comparing the integrated different signal with a threshold signal level, and providing an output signal indicative of capture upon the integrated difference signal exceeding the threshold level.

3. A system for detecting the responsiveness of a patient heart having a predetermined minimum refractory period to pacing pulses having a predetermined energy level, comprising:
   generating means electrically coupled to the heart for generating a series of pacing events signals, each comprising a pair of pulses each of said predetermined energy level separated in time by less than the refractory perod of the heart;
   detection means electrically coupled to the heart for detecting the artifact signal produced by the heart in response to each of said paired pulses; and
   comaprison means for comparing the artifact signal detected in response to the first pulse with the artifact signal detected in response to the second pulse of each pacing event signal to determine whether capture has occurred at the energy level of the pulses comprising that signal.

4. A system for detecting evoked cardiac contractions as defined in claim 3 including a pacing lead for coupling said generating means to the heart and the heart to said detection means.

5. A system for detecting evoked cardiac contractions as defined in claim 3 wherein said comparison means subtract the absolute values of the first and second artifact signals follwing each paving event to develop a difference signal indicative of capture occurrence.

6. A system for detecting evoked cardiac contractions as defined in claim 5 wherein said comparison means include threshold means for providing an output when said difference signal exceeds a predetermined threshold level.

7. A system for detecting evoked cardiac contractions as defined in claim 6 wherein said comparison means include integrating means for integrating said difference signal to develop a signal for application to said threshold means.

8. A system for detecting evoked cardiac contractions as defined in claim 3 wherein said comparison means include waveform memory means for storing at least one of aid artifact signals during each pacing event.

9. A system for detecting evoked cardiac contractions as defined in claim 8 wherein said comparison means include a first waveform memory means for storing the first artifact signal, a second waveform memory means for storing the second artifact signal and means for comparing the contacts of said memory means following each pacing event to develop said difference signal.

10. A system for detecting evoked cardiac contractions as defined in claim 3 wherein said pacing pulses are of equal amplitude.

11. A system for detecting the responsiveness of a patient heart having a predetermined minimum refractory period to pacing pulses having a predetermined energy level, comprising:
  generating means electrically coupled to the heart for generating a series of pacing event signals, each comprising a pair of pulses each of said predetermined energy level separated in time by less than the refractory period of the heart;
  detection means electrically coupled to the heart for detecting the artifact signal produced by the heart in response to each of said paired pulses; and
  first waveform storage means for storing the first artifact signal occurring during each pacing signal;
  second waveform storage means for storing the second artifact signal occurring during each pacing signal;
  subtraction means for subtracting following each pacing event the absolute values of the artifact signals stored in said first and second storage means to develop a different signal;
  integrating means for integrating said difference signal to develop an integrated different signal; and
  output circuit means for providing an output signal indicative of capture when said integrated difference signal exceeds a predetermined threshold level.

12. A system for detecting evoked cardiac contractions as defined in claim 11 including a pacing lead for coupling said generating means to the heart and the heart to said detection means.

13. A system for detecting evoked cardiac contractions as defined in claim 11 wherein said pacing pulses are of equal amplitude.

* * * * *

UNITED STATES PATENT AND TRADEMARK OFFICE
CERTIFICATE OF CORRECTION

PATENT NO. : 4,674,509
DATED : June 23, 1987
INVENTOR(S) : Robert DeCote, Jr.

It is certified that error appears in the above-identified patent and that said Letters Patent are hereby corrected as shown below:

Col. 2, line 20: Change "pace" to --pacer--.
line 25: After "events" insert --.--.
Col. 3, line 61: Change "respons" to --response--.
Col. 5, line 42: Change "t" to --to--.
Col. 7, line 33: Change "t" to --to--.
Col. 8, line 55: Change "syste" to --system--.
Col. 10, line 3: Change "puls" to --pulse--.
line 24: Change "withina" to --within a--.
line 56: Change "comaprison" to --comparison--.
Col. 11, line 18: Change "aid" to --said--.

UNITED STATES PATENT AND TRADEMARK OFFICE
CERTIFICATE OF CORRECTION

PATENT NO. : 4,674,509

DATED : June 23, 1987

INVENTOR(S) : Robert DeCote, Jr.

It is certified that error appears in the above-identified patent and that said Letters Patent are hereby corrected as shown below:

Col. 12, line 19: Change "different" to --difference--.

line 21: Change "different" to --difference--.

Signed and Sealed this

First Day of December, 1987

Attest:

DONALD J. QUIGG

Attesting Officer     Commissioner of Patents and Trademarks